(12) United States Patent
Gogyo

(10) Patent No.: US 10,283,810 B2
(45) Date of Patent: May 7, 2019

(54) LITHIUM-ION BATTERY

(71) Applicant: HITACHI CHEMICAL COMPANY, LTD., Tokyo (JP)

(72) Inventor: Yuma Gogyo, Tokyo (JP)

(73) Assignee: HITACHI CHEMICAL COMPANY, LTD., Tokyo (JP)

( * ) Notice: Subject to any disclaimer, the term of this patent is extended or adjusted under 35 U.S.C. 154(b) by 0 days.

(21) Appl. No.: 15/518,445

(22) PCT Filed: Oct. 16, 2015

(86) PCT No.: PCT/JP2015/079340
§ 371 (c)(1),
(2) Date: Apr. 11, 2017

(87) PCT Pub. No.: WO2016/060253
PCT Pub. Date: Apr. 21, 2016

(65) Prior Publication Data
US 2017/0309954 A1 Oct. 26, 2017

(30) Foreign Application Priority Data
Oct. 17, 2014 (JP) .................. 2014-212599

(51) Int. Cl.
H01M 10/052 (2010.01)
H01M 10/0525 (2010.01)
H01M 4/134 (2010.01)
H01M 4/485 (2010.01)
H01M 10/0567 (2010.01)
(Continued)

(52) U.S. Cl.
CPC ........... *H01M 10/0525* (2013.01); *C01F 5/04* (2013.01); *C01G 23/002* (2013.01); *C01G 45/006* (2013.01); *C01G 51/006* (2013.01); *H01M 4/134* (2013.01); *H01M 4/485* (2013.01); *H01M 4/505* (2013.01); *H01M 4/525* (2013.01); *H01M 10/0567* (2013.01); *H01M 2010/4292* (2013.01); *H01M 2300/0025* (2013.01)

(58) Field of Classification Search
CPC . H01M 10/052; H01M 10/0525; H01M 4/134
See application file for complete search history.

(56) References Cited

FOREIGN PATENT DOCUMENTS

JP 2001-210324 A 8/2001
JP 2005-317512 A 11/2005
(Continued)

OTHER PUBLICATIONS

International Search Report for PCT/JP2015/079340 dated Jan. 12, 2016; English translation submitted herewith (5 pages).
(Continued)

Primary Examiner — Karie O'Neill Apicella
(74) Attorney, Agent, or Firm — Fitch, Even, Tabin & Flannery, LLP

(57) ABSTRACT

A lithium-ion battery includes: a cathode; an anode; and a non-aqueous electrolyte solution, in which the cathode includes a current collector and a cathode mixture applied on at least one side of the current collector, the cathode mixture includes a lithium transition metal oxide as a cathode active material, the anode includes a lithium titanium complex oxide as an anode active material, and the non-aqueous electrolyte solution includes a fluorine-containing boric acid ester.

17 Claims, 2 Drawing Sheets

(51) Int. Cl.
   *C01G 23/00*   (2006.01)
   *C01G 45/00*   (2006.01)
   *C01G 51/00*   (2006.01)
   *C01F 5/04*    (2006.01)
   *H01M 4/505*   (2010.01)
   *H01M 4/525*   (2010.01)
   *H01M 10/42*   (2006.01)

(56) References Cited

FOREIGN PATENT DOCUMENTS

| | | | | |
|---|---|---|---|---|
| JP | 2012-124026 A | 6/2012 | | |
| JP | 2012-169138 A | 9/2012 | | |
| JP | 2012-174546 A | 9/2012 | | |
| JP | 2012174546 A | * 9/2012 | ........ | H01M 10/0569 |
| JP | 2014-112524 A | 6/2014 | | |
| WO | 2009/110490 A1 | 9/2009 | | |

OTHER PUBLICATIONS

Chemistry Dictionary Editorial Board, "Chemistry Dictionary 8 Reduced Edition", Reduced Edition, Nineteenth Issue, Kyoritsu Shuppan Co., Ltd., Sep. 10, 1976, p. 604 partial translation.

Office Action of Japanese Appln. No. 2016-554138 dated Jun. 20, 2017 with translation.

* cited by examiner

LITHIUM-ION BATTERY

CROSS-REFERENCE TO RELATED APPLICATIONS

This application is a U.S. national phase application filed under 35 U.S.C. § 371 of International Application No. PCT/JP2015/079340, filed Oct. 16, 2015, designating the United States, which claims priority from Japanese Patent Application No. 2014-212599, filed Oct. 17, 2014, which are hereby incorporated herein by reference in their entirety.

TECHNICAL FIELD

The present invention relates to a lithium-ion battery.

BACKGROUND ART

A lithium-ion battery is a secondary battery having a high energy density, and used as a power source for portable devices, such as a notebook computer or a cell phone, utilizing their characteristics.

In recent years, as a power source for electronic devices, a power source for power storage, and a power source for electric cars, for which downsizing is advancing, a demand for a lithium-ion battery superior in input-output properties, energy density, charge and discharge cycle performance, and storage stability at a high temperature has been growing.

As a means for improving output characteristics and charge and discharge cycle performance, technology pertaining to a lithium-ion battery using, as an node active material, a lithium-titanium complex oxide with a spinel structure having a certain specific surface area has been disclosed (see, for example, Japanese Patent Application Laid-Open (JP-A) No. 2005-317512).

Meanwhile, as a means for improving storage stability at a high temperature of a lithium-ion battery using a lithium titanium complex oxide as an anode active material, technology pertaining to a lithium-ion battery in which a non-aqueous electrolyte contains tris(trimethylsilyl) borate has been disclosed (see, for example, International Publication No. WO 2009/110490).

SUMMARY OF INVENTION

Technical Problem

However, through investigations by the inventors it has become clear that there is still room for improvement with respect to a lithium-ion battery according to International Publication No. WO 2009/110490, in which a non-aqueous electrolyte solution contains tris(trimethylsilyl) borate, in terms of high-temperature storage stability and cycle performance.

The present invention is made in view of the above circumstances and aims to provide a lithium-ion battery having superior charge and discharge cycle performance and superior storage stability at a high temperature.

Solution to Problem

The means for approaching the object includes the following embodiments.
<1> A lithium-ion battery, including:
  a cathode;
  an anode; and
  a non-aqueous electrolyte solution,
wherein the cathode includes a current collector and a cathode mixture coated on at least one side of the current collector,
wherein the cathode mixture includes a lithium transition metal oxide as a cathode active material,
wherein the anode includes a lithium-titanium complex oxide as an anode active material, and
wherein the non-aqueous electrolyte solution includes a fluorine-containing boric acid ester.
<2> The lithium-ion battery according to <1>, wherein the fluorine-containing boric acid ester includes a compound represented by the following Formula (a):

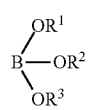

(a)

wherein, in Formula (a), each of $R^1$, $R^2$ and $R^3$ independently represents a hydrocarbon group having 1 to 10 carbon atoms, and at least one of $R^1$, $R^2$, or $R^3$ includes a fluorine atom.

Advantageous Effects of Invention

According to the invention, a lithium-ion battery having superior charge and discharge cycle performance and superior storage stability at a high temperature is provided.

DESCRIPTION OF EMBODIMENTS

Figure 1:
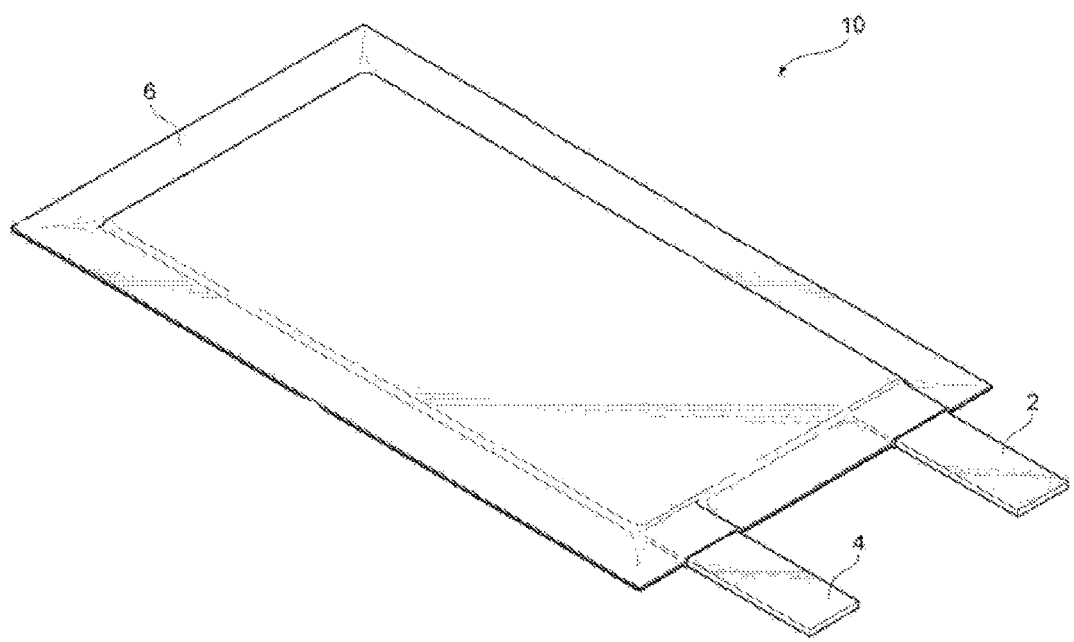
FIG. 1 is a perspective view schematically showing the overall structure of a lithium-ion battery according to an embodiment of the present invention.

As used herein, the term "step" includes not only a step independent from another step, but also a step which may not be clearly separated from another step, insofar as an intended function of the step can be attained.

In the specification, a numerical range expressed by "x to y" includes the values of x and y in the range as the minimum and maximum values, respectively.

With respect to numerical ranges stated hierarchically in the specification, the upper limit or the lower limit of a numerical range of a hierarchical level may be replaced with the upper limit or the lower limit of a numerical range of another hierarchical level, respectively. Further, with respect to a numerical range stated herein, the upper limit or the lower limit of the numerical range may be replaced with a relevant value stated in any of the Examples section.

In the specification, in referring to a content of a component in a composition, when plural kinds of substances exist corresponding to a component in the composition, the content means, unless otherwise specified, the total amount of the plural kinds of substances existing in the composition.

In the specification, in referring to a particle size of a component in a composition, when plural kinds of particles exist corresponding to a component in the composition, the particle size means, unless otherwise specified, a value with respect to the mixture of the plural kinds of particles existing in the composition.

As used herein, each of the terms "layer" or "film" encompasses not only a case in which the layer or film is formed over the entire region in which the layer or film is formed, but also a case in which the layer or film is formed only on a part of the region, when observed.

As used herein, the term "laminate" means to layer layers one on another, and two or more layers may be bonded together, or two or more layers may be layered detachably.

A lithium-ion battery according to an embodiment of the invention is a lithium-ion battery including: a cathode; an anode; and a non-aqueous electrolyte solution, wherein the cathode includes a current collector and a cathode mixture coated on at least one side of the current collector, the cathode mixture includes a lithium transition metal oxide as a cathode active material, the anode includes a lithium titanium complex oxide as an anode active material, and the non-aqueous electrolyte solution includes a fluorine-containing boric acid ester.

Since the lithium-ion battery according to an embodiment of the invention includes a lithium transition metal oxide as a cathode active material, and includes a lithium titanium complex oxide as an anode active material, the electric potential of the anode in which the insertion and elimination of a lithium-ion into/from the lithium titanium complex oxide occurs becomes 1.55 V with respect to a lithium electrode. Accordingly, reductive decomposition of an electrolyte solution, precipitation of metallic Li, and the like is suppressed, leading to improved safety. Furthermore, the battery also has superior lifetime property because there is no structure change due to the insertion and elimination.

Further, due to the inclusion of a non-aqueous electrolyte solution containing a fluorine-containing boric acid ester, the battery is superior in charge and discharge cycle performance, and storage stability at a high temperature. Although the reason behind the above is not clear, it is presumed as follows. A lithium salt (LiPF$_6$, etc.) included as an electrolyte is degraded by a reaction with a small amount of moisture contained in an electrolyte solution, reduction on an anode, or the like to form an inorganic material, such as LiF, and Li$_2$O. Such an inorganic material is formed on a surface of a LTO anode, and may cause increase in resistance or decrease in capacity. However, it is conceivable that a fluorine-containing boric acid ester contained in a non-aqueous electrolyte solution stabilizes a lithium salt thereby suppressing the degradation.

<Cathode>

A cathode is formed by coating a surface of a current collector with a cathode mixture, and, if necessary, by increasing the density of the applied cathode mixture by means of pressing or the like. The cathode mixture includes a cathode active material containing a lithium transition metal oxide and an electroconductive material, and includes, if necessary, a binder and a solvent.

Examples of a lithium transition metal oxide include Li$_x$CoO$_2$, Li$_x$NiO$_2$, Li$_x$MnO$_2$, Li$_x$Co$_y$Ni$_{1-y}$O$_2$, Li$_x$Co$_y$M$_{1-y}$O$_z$, Li$_x$Ni$_{1-y}$M$_y$O$_z$, Li$_x$Mn$_2$O$_4$, and Li$_x$Mn$_{2-y}$M$_y$O$_4$ (in the respective formulas, M represents at least one element selected from the group consisting of Na, Mg, Sc, Y, Mn, Fe, Co, Ni, Cu, Zn, Al, Cr, Pb, Sb, V, and B; x=0 to 1.2; y=0 to 0.9; and z=2.0 to 2.3). The value x, which represents the molar ratio of lithium, increases or decreases by charge and discharge.

The lithium transition metal oxide is preferably a lithium transition metal oxide containing manganese from the viewpoint of safety, energy density, and higher capacity.

As a lithium transition metal oxide containing manganese, a spinel lithium manganese oxide (sp-Mn) is preferable from the viewpoint of further improvement of safety. Meanwhile, from the viewpoint of attaining higher capacity, a layered lithium-nickel-manganese-cobalt complex oxide (NMC) is preferable.

From the viewpoint of both of safety and higher capacity, it is preferable to use a combination of a spinel lithium manganese oxide (sp-Mn) and a layered lithium-nickel-manganese-cobalt complex oxide (NMC).

From the viewpoint of increasing energy density to a higher level, a lithium-manganese-nickel complex oxide (LNMO), which is capable of increasing the electric potential of a cathode, is preferable.

It is preferable that the spinel lithium manganese oxide (sp-Mn) be that represented by the following compositional formula (1).

$$Li_{(1+\eta)}Mn_{(2-\lambda)}M'_\lambda O_2 \quad (2)$$

In the compositional formula (1), $-0.2 \leq \eta \leq 0.2$, and $0 \leq \lambda \leq 1$.

In the compositional formula (1), $(1+\eta)$ is the composition ratio of Li, $(2-\lambda)$ is the composition ratio of Mn, and k is the composition ratio of an element M', respectively. The composition ratio of O (oxygen) is 4.

The element M' is at least one element selected from the group consisting of Mg (magnesium), Ca (calcium), Sr (strontium), Al, Ga, Zn (zinc), Ti, Cr, Fe, Co, and Cu (copper).

It is preferable that the layered lithium nickel manganese cobalt complex oxide (NMC) be that represented by the following compositional formula (2).

$$Li_{(1+\delta)}Mn_xNi_yCo_{(1-x-y-z)}M_zO_2 \quad (2)$$

In the compositional formula (2), $-0.15 < \delta < 0.15$, $0.1 < x \leq 0.5$, $0.6 < x+y+z \leq 1.0$, and $0 \leq z \leq 0.1$.

In the compositional Formula (2), $(1+\delta)$ is the composition ratio of Li (lithium), x is the composition ratio of Mn (manganese), y is the composition ratio of Ni (nickel), and $(1-x-y-z)$ is the composition ratio of Co (cobalt), respectively. Furthermore, z is the composition ratio of an element M. The composition ratio of O (oxygen) is 2.

The element M is at least one element selected from the group consisting of Ti (titanium), Zr (zirconium), Nb (niobium), Mo (molybdenum), W (tungsten), Al (aluminum), Si (silicon), Ga (gallium), Ge (germanium), and Sn (tin).

Examples of the layered lithium nickel manganese cobalt complex represented by compositional formula (2) include LiNi$_{0.5}$Mn$_{0.3}$Co$_{0.2}$O$_2$, and LiNi$_{1/3}$Mn$_{1/3}$Co$_{1/3}$O$_2$.

The lithium manganese nickel complex oxide is preferably a lithium manganese nickel complex oxide having a spinel structure. The spinel lithium manganese nickel complex oxide is a compound represented by the compositional formula of LiNi$_x$Mn$_{2-x}$O$_4$ (in which $0.1 < X < 1.1$).

From the viewpoint of stability, LiNi$_{0.5}$Mn$_{1.5}$O$_4$ is more preferable. For stabilizing further the crystal structure of LiNi$_{0.5}$Mn$_{1.5}$O$_4$ having a spinel structure, a spinel lithium manganese nickel complex oxide, in which a part of Mn/Ni sites are replaced with other metal atom(s), in which excessive lithium is made present in a crystal, or in which a defect is generated in an O site, may be used.

Examples of other metal atom(s) which is/are capable of substituting a Mn/Ni site include Ti, V, Cr, Fe, Co, Zn, Cu, W, Mg, Al, and Ru. The metal atoms may be used singly or in a combination of two or more kinds thereof. Among the substitutable metal elements, Ti is preferable from the viewpoint of stabilization of a crystal structure.

The lithium manganese nickel complex oxide is preferably used at an electric potential in a charged state of from 4.5 V to 5 V, and more preferably from 4.6 to 4.9 V, with respect to Li/Li$^+$, from the viewpoint of high energy density.

A layered lithium nickel manganese cobalt complex oxide (NMC) and a spinel lithium manganese oxide (sp-Mn) are each preferably in a form of particle. When the cathode active materials are in a form of particle, the BET specific surface area of the particle may be, for example, 0.2 m$^2$/g or more, and is preferably 0.3 m$^2$/g or more, and more preferably 0.4 m$^2$/g or more. The BET specific surface area of the particle may be, for example, 4.0 m$^2$/g or less, and is preferably 2.5 m$^2$/g or less, and more preferably 1.5 m$^2$/g or less.

The lithium manganese nickel complex oxide (LNMO) is preferably in a form of particle. When the lithium manganese nickel complex oxide is in a form of particle, the BET specific surface area of the particle is preferably less than 1 m$^2$/g, more preferably less than 0.5 m$^2$/g, and further preferably less than 0.3 m$^2$/g, from the viewpoint of further improvement of storage stability at a high temperature. The BET specific surface area is preferably 0.05 m$^2$/g or more, more preferably 0.08 m$^2$/g or more, and further preferably 0.1 m$^2$/g or more, from the viewpoint of improvement of input-output characteristics (hereinafter also referred to as "rate performance").

The BET specific surface area may be measured, for example, based on a nitrogen adsorption capacity according to JIS Z 8830. As a measuring apparatus, for example, an AUTOSORB-1 (trade name) available from Quantachrome Instruments may be used. When a BET specific surface area is to be measured, it is preferable to conduct a pretreatment for removing moisture by heating in advance, since moisture adsorbed on a surface of a sample or the inside thereof may conceivably influence the gas adsorption capacity. In the pretreatment, it is preferable that a measurement cell loaded with 0.05 g of a sample for measurement is evacuated using a vacuum pump to 10 Pa or less, and then heated at 110° C. for 3 hours or longer, followed by cooling naturally to normal temperature (25° C.) while maintaining the reduced pressure. After the pretreatment, it is preferable that the measurement is conducted under the conditions of a measurement temperature of 77K (−196.15° C.) and a measurement pressure range of less than 1 in terms of relative pressure (equilibrium pressure with respect to saturated vapor pressure).

When the lithium manganese nickel complex oxide (LNMO) is in a form of particle, the median diameter D50 (or the median diameter D50 of the secondary particle in a case in which primary particles aggregate to form a secondary particle) is preferably from 0.5 μm to 100 μm, and more preferably from 1 μm to 50 μm, from the viewpoint of dispersibility in a cathode mixture. In this regard, the median diameter D50 may be determined from a particle size distribution obtained by a laser diffraction scattering method.

When the lithium transition metal oxide is used, the content thereof with respect to the total amount of a cathode active material is from 50% by mass to 100% by mass, more preferably from 60% by mass to 100% by mass, and further preferably from 80% by mass to 100% by mass, from the viewpoint of improvement of battery capacity.

When the lithium manganese nickel complex oxide (LNMO) among the above-mentioned lithium transition metal oxides is used, the content thereof with respect to the total amount of a cathode active material is preferably from 60% by mass to 100% by mass, more preferably from 70% by mass to 100% by mass, and further preferably from 85% by mass to 100% by mass, from the viewpoint of improvement of battery capacity.

As an electroconductive material, one of or two or more of carbon substance powders including a carbon black, such as acetylene black or Ketjenblack, graphite, and the like may be used from the viewpoint of improvement of the electric conductivity of a cathode. Furthermore, the electroconductive material may additionally contain a small amount of carbon nanotube, graphene, or the like in order to improve the electric conductivity of a cathode.

The electroconductive material is preferably acetylene black from the viewpoint of improvement of rate performance. The content of the electroconductive material with respect to the total amount of a cathode mixture is preferably 4% by mass or more, more preferably 5% by mass or more, and further preferably 5.5% by mass or more, from the viewpoint of rate performance. Regarding the upper limit, the content of the electroconductive material with respect to the total amount of a cathode mixture is preferably 10% by mass or less, more preferably 9% by mass or less, and further preferably 8.5% by mass or less, from the viewpoint of battery capacity.

The binder is not particularly limited, and a material having superior solubility or dispersibility in a dispersing solvent is selected as the binder. Specific examples thereof include: a resin polymer such as polyethylene, polypropylene, poly(ethylene terephthalate), poly(methyl methacrylate), polyimide, aromatic polyamide, cellulose, or nitrocellulose; a rubber polymer such as SBR (styrene-butadiene rubber), NBR (acrylonitrile-butadiene rubber), fluorocarbon rubber, isoprene rubber, butadiene rubber, or ethylene-propylene rubber; a thermoplastic elastomer polymer such as a styrene-butadiene-styrene block copolymer or a hydrogenated product thereof, an EPDM (ethylene-propylene-diene terpolymer), a styrene-ethylene-butadiene-ethylene copolymer, or a styrene-isoprene-styrene block copolymer or a hydrogenated product thereof; a soft resin polymer such as syndiotactic 1,2-polybutadiene, poly(vinyl acetate), an ethylene-vinyl acetate copolymer, or a propylene-α-olefin copolymer; a fluorocarbon polymer, such as poly(vinylidene fluoride) (PVdF), polytetrafluoroethylene, fluorinated poly(vinylidene fluoride), a polytetrafluoroethylene-ethylene copolymer, or a polytetrafluoroethylene-vinylidene fluoride copolymer; a copolymer obtained by adding acrylic acid and a straight chain ether group to a polyacrylonitrile skeleton; and a polymer composition having ion conductivity of an alkali metal ion (especially lithium ion). The binders may be used singly, or in a combination of two or more thereof. From the viewpoint of high adherence of a cathode, use of poly(vinylidene-fluoride) (PVdF), or a copolymer obtained by adding acrylic acid and a straight chain ether group to a polyacrylonitrile skeleton is preferable.

The range of the content of a binder with respect to the mass of a cathode mixture is as follows. Regarding the lower limit, the content is preferably 0.1% by mass or more, more preferably 1% by mass or more, and further preferably 2% by mass or more, from the viewpoint of achievement of adequate binding of a cathode active material to obtain adequate mechanical strength of a cathode and to stabilize battery performance such as cycle performance. Regarding the upper limit, the content is preferably 30% by mass or less, more preferably 20% by mass or less, and further preferably 10% by mass or less, from the viewpoint of improvement of battery capacity and electrical conductivity.

The solvent used for dispersing a cathode active material, an electroconductive material, a binder, or the like is not particularly limited, and an organic solvent such as N-methyl-2-pyrrolidone may be used as the solvent.

The material of a current collector is not particularly limited. Examples thereof include aluminum, titanium, stainless steel, nickel, baked carbon, electrically conductive polymer, and electrically conductive glass. Furthermore, a metallic foil of aluminum, copper, or the like, on which surface has been subjected to a treatment such as coating with carbon, nickel, titanium, silver, or the like, for the purpose of improvement of adhesiveness, electrical conductivity, or oxidation resistance, may be used as the material of a current collector. The thickness of a current collector is not particularly limited. The thickness of a current collector is preferably from 1 μm to 50 μm from the viewpoint of the strength of electrode and energy density.

The coating amount (on a single side) of a cathode mixture on a current collector is preferably from 10 g/m$^2$ to 250 g/m$^2$, and more preferably from 50 g/m$^2$ to 200 g/m$^2$, from the viewpoint of energy density and input-output characteristics. The density of a cathode mixture is preferably from 1.8 g/cm$^3$ to 3.2 g/cm$^3$, and more preferably from 2.0 g/cm$^3$ to 3.0 g/cm$^3$, from the viewpoint of energy density and rate performance.

<Anode>

An anode is formed by coating a surface of a current collector with an anode mixture, and, if necessary, by increasing the density of the applied anode mixture by means of pressing or the like. The anode mixture includes an anode active material containing a lithium titanium complex oxide and an electroconductive material, and includes, if necessary, a binder and a solvent.

The anode active material may be solely composed of a lithium titanium complex oxide. However, the anode active material may further contain another substance capable of functioning as an anode active material, such as a carbon material, for the purpose of improvement of characteristics of a lithium-ion battery, or the like.

The lithium titanium complex oxide (LTO) is preferably a lithium titanium complex oxide having a spinel structure. A basic compositional formula for a spinel lithium titanium complex oxide is expressed as $Li[Li_{1/3}Ti_{5/3}]O_4$. For stabilizing further the crystal structure, a part of Li or Ti sites may be substituted with other metal atom(s), excessive lithium may be made present in a crystal, or a part of O sites may be substituted with other element(s). Examples of other metal atom(s) which may be used for substitution, include F, B, Nb, V, Mn, Ni, Cu, Co, Zn, Sn, Pb, Al, Mo, Ba, Sr, Ta, Mg, and Ca. The metal atoms may be used singly, or in a combination of two or more kinds.

The content of a lithium titanium complex oxide with respect to the total amount of an anode active material is preferably from 70% by mass to 100% by mass, more preferably from 80% by mass to 100% by mass, and further preferably from 90% by mass to 100% by mass, from the viewpoint of improvement of safety and cycle performance.

Examples of the electroconductive material include the electroconductive materials which may be used for a cathode, and preferable examples of the electroconductive material are also the same as those mentioned in relation with the cathode. From the viewpoint of further improvement of rate performance, acetylene black is preferable. The content of an electroconductive material with respect to the total amount of an anode mixture is preferably 1% by mass or more, more preferably 4% by mass or more, and further preferably 6% by mass or more, from the viewpoint of rate performance. Regarding the upper limit, the content of an electroconductive material with respect to the total amount of an anode mixture is preferably 15% by mass or less, more preferably 12% by mass or less, and further preferably 10% by mass or less, from the viewpoint of battery capacity.

Examples of the binder include the binders which may be used for a cathode. The content of a binder with respect to the total amount of an anode mixture is as follows. Regarding the lower limit of the range, the content is preferably 0.1% by mass or more, more preferably 0.5% by mass or more, and further preferably 1% by mass or more, from the viewpoint that an anode active material is bonded adequately to exhibit adequate mechanical strength of an anode, and that the battery performances, such as cycle performance, are stabilized. Regarding the upper limit, the content is preferably 40% by mass or less, more preferably 25% by mass or less, and further preferably 15% by mass or less, from the viewpoint of improvement of battery capacity and electrical conductivity.

The solvent used for dispersing an anode active material, an electroconductive material, a binder, or the like is not particularly limited, and an organic solvent such as N-methyl-2-pyrrolidone may be used as the solvent.

The material of a current collector is not particularly limited. Examples thereof include copper, stainless steel, nickel, aluminum, titanium, baked carbon, an electrically conductive polymer, an electrically conductive glass, and an aluminum-cadmium alloy. Furthermore, a metallic foil of copper, aluminum, or the like, on which surface has been subjected to a treatment such as coating with carbon, nickel, titanium, silver, or the like, for the purpose of improvement of adhesiveness, electrical conductivity, or resistance to reduction, may be used. The thickness of a current collector is not particularly limited. The thickness of a current collector is preferably from 1 μm to 50 μm from the viewpoint of the strength of electrode and energy density.

The coating amount (on a single side) of an anode mixture on a current collector is preferably from 10 g/m$^2$ to 200 g/m$^2$, and more preferably from 50 g/m$^2$ to 150 g/m$^2$, from the viewpoint of energy density and input-output characteristics. The density of an anode mixture is preferably from 1.0 g/cm$^3$ to 2.8 g/cm$^3$, and more preferably from 1.2 g/cm$^3$ to 2.6 g/cm$^3$, from the viewpoint of energy density and rate performance.

<Non-Aqueous Electrolyte Solution>

The non-aqueous electrolyte solution is a non-aqueous solvent having dissolved an electrolyte therein. A non-aqueous electrolyte solution according to an embodiment of the invention contains a fluorine-containing boric acid ester. The fluorine-containing boric acid esters may be used singly, or in a combination of two or more kinds.

It is preferable that the fluorine-containing boric acid ester is, for example, a compound represented by the following Formula (a).

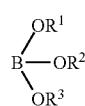

(a)

In Formula (a), each of R$^1$, R$^2$ and R$^3$ independently represents a hydrocarbon group having 1 to 10 carbon atoms, and at least one of R$^1$, R$^2$ or R$^3$ contains a fluorine atom.

The hydrocarbon group represented by R$^1$, R$^2$, or R$^3$ in Formula (a) independently has preferably 1 to 6 carbon atoms, more preferably 1 to 5 carbon atoms, and further preferably 1 to 3 carbon atoms, from the viewpoint of solubility in an electrolyte solution.

The hydrocarbon group represented by $R^1$, $R^2$, or $R^3$ in Formula (a) independently has preferably 0 to 21 fluorine atoms, more preferably 0 to 13 fluorine atoms, further preferably 0 to 11 fluorine atoms, and still further preferably 0 to 7 fluorine atoms.

From the viewpoint of improvement of cycle performance and high-temperature cycle performance, it is preferable that two or more hydrocarbon groups among the hydrocarbon groups represented by $R^1$, $R^2$, and $R^3$ in Formula (a) each contain a fluorine atom, and more preferable that all of the three hydrocarbon groups each contain a fluorine atom.

Examples of a hydrocarbon group represented by $R^1$, $R^2$, or $R^3$ in Formula (a) include a straight-chain alkyl group, a cyclic alkyl group, a branched alkyl group, an aryl group, and a hydrocarbon group with a configuration in which an alkyl group and an aryl group are bonded. Specific examples thereof include a methyl group, an ethyl group, a n-propyl group, an isopropyl group, a 2-methylpropyl group, a phenyl group, and 2-phenylpropyl.

Specific examples of a fluorine-containing hydrocarbon group which is represented by $R^1$, $R^2$, or $R^3$ in Formula (a) include a trifluoroethyl group, a tetrafluoroethyl group, a monofluoroethyl group, a pentafluoropropyl group, a hexafluoropropyl group, a hexafluoroisopropyl group, a 1,1,1,3,3,3-hexafluoro-2-methylpropyl group, a 1,1,1,3,3,3-hexafluoro-2-phenylpropyl group, a tetrafluorophenyl group, and a pentafluorophenyl group.

Examples of a compound represented by Formula (a) include tris(trifluoroethyl) borate, methyl bis(trifluoroethyl) borate, tris(tetrafluoroethyl) borate, tris(monofluoroethyl) borate, tris(pentafluoropropyl) borate, tris(hexafluoropropyl) borate, tris(hexafluoroisopropyl) borate, tris(2-methyl-1,1,1,3,3,3-hexafluoropropyl) borate, tris(2-phenyl-1,1,1,3,3,3-hexafluoropropyl) borate, and tris(pentafluorophenyl) borate. The compounds may be used singly, or in a combination of two or more kinds.

Among the compounds each represented by Formula (a), tris(hexafluoroisopropyl) borate, tris(trifluoroethyl) borate such as tris(2,2,2-trifluoroethyl) borate, and tris(pentafluorophenyl) borate are preferable from the viewpoint of improvement of cycle performance and high-temperature cycle performance, and tris(hexafluoroisopropyl) borate is more preferable.

The content of the fluorine-containing boric acid ester in a non-aqueous electrolyte solution with respect to the total amount of the non-aqueous electrolyte solution is preferably from 0.02% by mass to 10% by mass, more preferably from 0.05% by mass to 5% by mass, further preferably from 0.05% by mass to 4% by mass, and especially preferably from 0.1% by mass to 3% by mass, from the viewpoint of cycle performance and storage stability at a high temperature.

Examples of an electrolyte to be contained in a non-aqueous electrolyte solution include lithium salts. Examples of lithium salts include $LiPF_6$, $LiBF_4$, LiFSI (lithium bis(fluorosulfonyl)imide), LiTFSI (lithium bis(trifluoromethanesulfonyl)imide), $LiClO_4$, $LiB(C_6H_5)_4$, $LiCH_3SO_3$, $LiCF_3SO_3$, $LiN(SO_2F)_2$, $LiN(SO_2CF_3)_2$, and $LiN(SO_2CF_2CF_3)_2$. The lithium salts may be used singly, or in a combination of two or more kinds.

Among the lithium salts, lithium hexafluorophosphate ($LiPF_6$) is preferable from the viewpoint of balance between solubility in a solvent, charge and discharge characteristics when assembled into a lithium-ion battery, input-output characteristics, cycle performance, and the like.

The concentration of an electrolyte with respect to the non-aqueous solvent is preferably from 0.5 mol/L to 1.5 mol/L, more preferably from 0.7 mol/L to 1.3 mol/L, and further preferably from 0.8 mol/L to 1.2 mol/L. When the concentration of a lithium salt is from 0.5 mol/L to 1.5 mol/L, charge and discharge characteristics may be further improved.

The non-aqueous solvent is not particularly limited. Examples thereof include: a cyclic carbonate such as ethylene carbonate or propylene carbonate; a chain carbonate such as methyl carbonate, diethyl carbonate, or ethyl methyl carbonate; γ-butyrolactone; acetonitrile; 1,2-dimethoxyethane; dimethoxymethane; tetrahydrofuran; dioxolane; methylene chloride; and methyl acetate. Although the non-aqueous solvents may be used singly or in a combination of two or more kinds thereof, use of a combination of a cyclic carbonate and a chain carbonate is preferable.

When the non-aqueous solvent contains a cyclic carbonate, the content of the cyclic carbonate with respect to the total amount of a non-aqueous solvent is preferably from 10% by volume to 70% by volume, more preferably from 15% by volume to 60% by volume, and further preferably from 20% by volume to 55% by volume.

The non-aqueous electrolyte solution may further contain an additive other than the fluorine-containing boric acid ester, for the purpose of improving storage stability at a high temperature, cycle performance, input-output characteristics, or the like. The type of the additive is not particularly limited, and may be selected according to the object. Examples thereof include a heterocyclic compound containing at least one selected from the group consisting of a nitrogen atom and a sulfur atom, a cyclic carboxylic acid ester, a fluorine-containing cyclic carbonate, and other compounds having an unsaturated bond in a molecule thereof.

The non-aqueous electrolyte solution may further contain additives other than those mentioned above, such as an overcharge prevention material, an anode film forming material, a cathode protection material, or a high input-output material, depending on the required function.

<Separator>

A lithium-ion battery according to an embodiment of the invention preferably includes, in addition to a cathode, an anode, and a non-aqueous electrolyte solution, a separator arranged between the cathode and the anode.

The separator is not particularly limited as long as it has ion permeability while electrically insulating between the cathode and the anode, and it has resistance to oxidation on the cathode side and resistance to reduction on the anode side. Examples of the materials for a separator satisfying such properties include a resin, an inorganic material, and a glass fiber.

Examples of the resin include an olefin polymer, a fluoropolymer, a cellulose polymer, a polyimide, and a nylon. From the viewpoint of superior chemical stability and liquid retentivity, a porous sheet, a nonwoven fabric, or the like formed from a polyolefin, such as polyethylene or polypropylene, as a source material, are preferably used as a separator.

Examples of the inorganic material include: an oxide such as alumina or silicon dioxide; a nitride such as aluminum nitride or silicon nitride; and a sulfate such as barium sulfate or calcium sulfate. For example, a substrate in a form of thin film, such as a nonwoven fabric, a woven fabric, or a microporous film, to which the inorganic material in a fiber form or a particle form is adhered, may be used as a separator. As a substrate in a form of thin film, one having a pore size of from 0.01 μm to 1 μm, and a thickness of from 5 μm to 50 μm may be used favorably. Further, a composite porous layer formed from the inorganic material, for example, in a in a fiber form or a particle form and a binder such as a resin, may be used as a separator. Furthermore, the composite porous layer may be formed on a surface of a cathode or an anode as a separator. For example, a composite porous layer, to which alumina particles having a 90% average particle diameter (D90) of less than 1 μm has been bonded using a fluorocarbon resin as a binder, may be formed on a surface of a cathode or an anode, or on a separator surface facing a cathode or an anode.

<Overall Structure of Lithium-ion Secondary Battery>

The shape of a lithium-ion battery according to an embodiment of the invention is not particularly limited, and may be selected from various shapes such as cylindrical, laminated, or coin-shaped shape. Any type of lithium-ion batteries is configured in such a manner that an electrode body having a structure in which a cathode and an anode are laminated (if necessary, a separator is arranged between the cathode and the anode), is contained together with a non-aqueous electrolyte solution in a hermetically closed battery case. A cathode current collector and an anode current collector are respectively connected with a cathode terminal and an anode terminal, which communicate with the outside of the battery, by collector leads or the like.

Hereinbelow, a laminated lithium-ion battery having an electrode body in which a cathode and an anode are layered via a separator is described as an exemplary embodiment of the invention, with reference to the drawings. The sizes, shapes, and the like of the respective components shown in FIG. 1 and FIG. 2 may be selected arbitrarily, and not limited to the specific examples shown in FIG. 1 and FIG. 2. The embodiments of the invention are not limited to those shown in the drawings, and may be, for example, a wound-type lithium-ion battery having an electrode body, in which a cathode and an anode are layered via a separator, is spirally wound.

FIG. 1 is a perspective view schematically showing an overall structure of a laminated lithium-ion secondary battery. A lithium-ion battery 10 has a configuration in which an electrode body and a non-aqueous electrolyte solution are arranged in a battery container formed from a laminate film 6, and a cathode collector tab 2 connected with a cathode and an anode collector tab 4 connected with an anode extend outward from the battery container.

Figure 2:
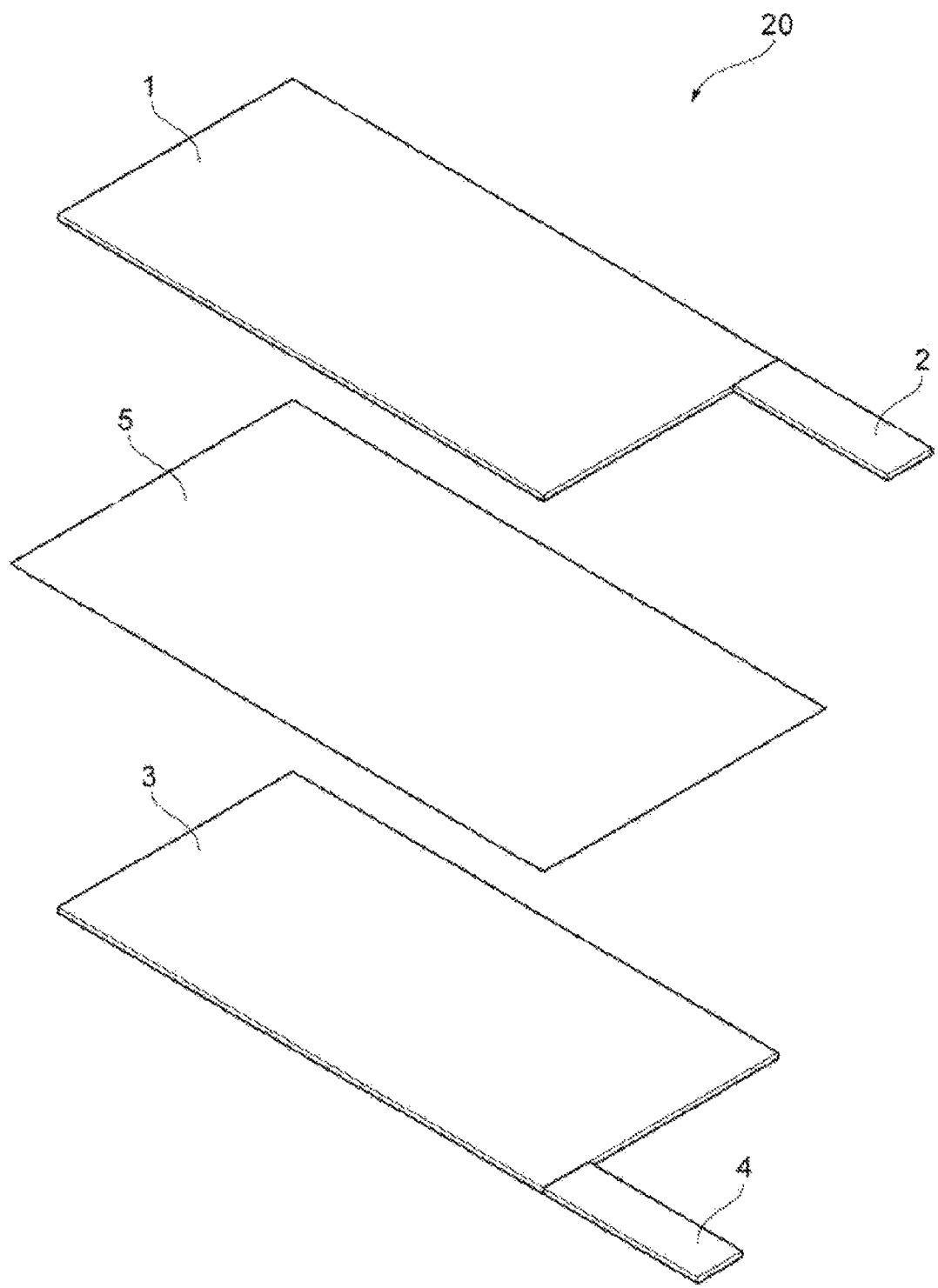
FIG. 2 is a perspective view schematically showing the structure of an electrode body.

FIG. 2 is a perspective view schematically showing the structure of an electrode body. An electrode body 20 has a configuration in which a cathode 1 provided with the cathode collector tab 2, a separator 5, and an anode plate 3 provided with the anode collector tab 4 are laminated in this order.

<Capacity Ratio of Anode to Cathode>

The capacity ratio of an anode to a cathode (i.e., anode capacity/cathode capacity) according to an embodiment of the invention is preferably 0.7 or more and less than 1.5, more preferably from 0.75 to 1.2, and further preferably from 0.90 to 1.1, from the viewpoint of safety and energy density.

When the lithium manganese nickel complex oxide mentioned above is used as a cathode active material, the capacity ratio of an anode to a cathode (i.e., anode capacity/cathode capacity) is preferably 0.7 or more and less than 1. When the capacity ratio of an anode to a cathode is 0.7 or more, the battery capacity tends to increase, and a higher energy density tends to be obtained. When the capacity ratio of an anode to a cathode is less than 1, a degradation reaction of a fluorine-containing boric acid ester due to the increase in an electric potential of a cathode tends to be suppressed, and the cycle performance of a lithium-ion battery tends to be improved.

Each of the "cathode capacity" and "anode capacity" mentioned above means a maximum capacity which is obtained reversibly, when an electrochemical cell in which metal lithium is used as a counter electrode of the cathode or anode is subjected to constant current/constant voltage charge and constant current discharge.

For example, in a case in which LNMO is used as a cathode active material, and LTO is used as an anode active material, a "cathode capacity" and an "anode capacity" are capacities obtained by evaluation when the charge and discharge was performed with respect to the electrochemical cell under the conditions of a voltage range between 4.95 V and 3.5 V, and a voltage range between 2 V and 1 V, respectively, and a current density of 0.1 mA/cm$^2$ during constant current charge and constant current discharge.

In a case in which a mixture of sp-Mn and NMC is used as a cathode active material, and LTO is used as an anode active material, a "cathode capacity" and an "anode capacity" are capacities obtained by evaluation when the charge and discharge was performed with respect to the electrochemical cell under the conditions of a voltage range between 3.0 V and 4.3 V, and a voltage range between 2 V and 1 V, respectively, and a current density of 0.1 mA/cm$^2$ during constant current charge and constant current discharge.

Although an embodiment of a lithium-ion battery according to the invention is described above, the embodiment is only an example, and may be implemented in various modes incorporating various modifications or improvements in the embodiment devised based on the knowledge of those skilled in the art.

EXAMPLES

Hereinbelow, the embodiments of the invention are described in more detail by way of examples. It is noted that the invention be not restricted in any way by the following examples.

Examples 1 to 3, and Comparative Examples 1 to 4

(Production of Cathode)

First, a cathode active material mixture was obtained by mixing cathode active materials of a layered lithium nickel manganese cobalt complex oxide (NMC) and a spinel lithium-manganese oxide (sp-Mn) at a mass ratio of 3/7 (NMC/sp-Mn). Then, 90 parts by mass of the cathode active material mixture, 5 parts by mass of acetylene black (available from Denka Company Limited) as an electroconductive material, and 5 parts by mass of poly(vinylidene fluoride) as a binder were mixed, and an appropriate amount of N-methyl-2-pyrrolidone was added thereto, followed by kneading, to thereby prepare a pasty cathode mixture (i.e., a cathode mixture paste). The cathode mixture was applied on one side of a 20 μm-thick aluminum foil, which was a current collector for a cathode, in a weight of 195 g/m$^2$. The coated aluminum foil was then subjected to a drying treatment, and subjected to a pressing treatment so that the density of the applied cathode mixture became 2.55 g/cm$^3$, to thereby prepare a sheet-formed cathode. The thus-prepared cathode was cut into a rectangle of 31 mm wide by 46 mm long, to which a cathode collector tab was then attached at the position indicated in FIG. 2.

(Production of Anode)

First, 91 parts by mass of lithium titanate (LTO) as an anode active material, 4 parts by mass of acetylene black (available from Denka Company Limited) as an electroconductive material, and 5 parts by mass of poly(vinylidene fluoride) as a binder were mixed, and an appropriate amount of N-methyl-2-pyrrolidone was added thereto, followed by kneading, to thereby prepare a pasty anode mixture (i.e., an anode mixture paste). The anode mixture was applied on one side of a 10 μm-thick copper foil, which was a current collector for an anode, in a weight of 85 g/m². The coated copper foil was then subjected to a drying treatment, and subjected to a pressing treatment so that the density of the applied anode mixture became 1.9 g/cm³, to thereby prepare a sheet-formed anode. The thus-prepared anode was cut into a rectangle of 30 mm wide by 45 mm long, to which an anode collector tab was then attached at the position indicated in FIG. 2.

(Production of Electrode Body)

An electrode body was produced by laminating the thus-prepared cathode, a polyethylene microporous membrane as a separator, and the thus-prepared anode in this order. The polyethylene microporous membrane has a dimension of 30 μm in thickness, 35 mm in width, and 50 mm in length.

The cathode and the anode were arranged in such a manner that a side of the cathode on which the cathode active material had been applied faced a side of the anode on which the anode active material had been applied to each other via the separator.

(Preparation of Non-Aqueous Electrolyte Solution)

A non-aqueous solvent was prepared by mixing ethylene carbonate and dimethyl carbonate at a volume ratio (i.e., ethylene carbonate:dimethyl carbonate) of 3:7. Next, $LiPF_6$ as an electrolyte was dissolved in the non-aqueous solvent, and the concentration of the electrolyte was adjusted to 1.0 mol/L. Then, an additive as shown in Table 1 was added thereto, to thereby prepare a non-aqueous electrolyte solution. The amount of the additive was adjusted to achieve the content (with respect to the total non-aqueous electrolyte solution as 100% by mass) as shown in Table 1.

(Production of Lithium-Ion Battery)

The electrode body produced as described above was placed in a battery container as shown in FIG. 1, and 1 mL of the non-aqueous electrolyte solution prepared as above was then charged therein. Thereafter, the opening of the battery container was closed in a state in which the edges of the cathode collector tab and the anode collector tab of the electrode body protruded outside, to thereby produce a lithium-ion battery. As the battery container, a battery container made from a laminate film consisting of a poly(ethylene terephthalate) (PET) film/an aluminum foil/a sealant layer (such as polypropylene or the like) was used. Two lithium-ion batteries were produced for each example and comparative example for the purpose of evaluation of cycle performance and storage stability at a high temperature described below.

(Cycle Performance)

The lithium-ion battery was subjected to constant current charge at 25° C. with a current value of 0.2 C to a charge cut-off voltage of 3.1 V, followed by constant voltage charge with a charge voltage of 3.1 V until the current value reached 0.01 C, using a charge and discharge apparatus (i.e., BATTERY TEST UNIT, available from IEM). In this regard, "C" used as a unit for a current value means [current (A)/battery capacity (Ah)]. After a pause of 15 minutes, constant current discharge was conducted with a current value of 0.2 C, and a discharge cut-off voltage of 1.5 V. Charge and discharge under the charging and discharging conditions mentioned above was repeated 3 times. Thereafter, constant current charge was conducted at 25° C. with a current value of 1 C and a charge cut-off voltage of 3.1 V, followed by constant voltage charge with a charge voltage of 3.1 V until the current value reached 0.01 C. After a pause of 15 minutes, constant current discharge was conducted with a current value of 1 C and a discharge cut-off voltage of 1.5 V. The discharge capacity at this time was regarded as the initial discharge capacity. Additionally, a discharge capacity was measured after repeating the above operations 500 times (discharge capacity after 500 cycles). Then, a cycle performance (i.e., deterioration rate after 500 cycles) was calculated according to the following equation. The measurement result is shown in Table 1.

Cycle performance (%)=(discharge capacity after 500 cycles/initial discharge capacity)×100

(Storage Stability at High Temperature)

The lithium-ion battery was subjected to constant current charge at 25° C. with a current value of 0.2 C to a charge cut-off voltage of 3.1 V, followed by constant voltage charge with a charge voltage of 3.1 V until the current value reached 0.01 C, using a charge and discharge apparatus (BATTERY TEST UNIT, produced by IEM). After a pause of 15 minutes, constant current discharge was conducted with a current value of 0.2 C and a discharge cut-off voltage of 1.5 V. Charge and discharge under the charging and discharging conditions mentioned above was repeated 3 times. Thereafter, constant current charge was conducted at 25° C. with a current value of 1 C and a charge cut-off voltage of 3.1 V, followed by constant voltage charge with a charge voltage of 3.1 V until the current value reached 0.01 C. After a pause of 15 minutes, constant current discharge was conducted with a current value of 1 C and a discharge cut-off voltage of 1.5 V. The discharge capacity at this time was regarded as the initial discharge capacity.

Next, constant voltage charge was performed with a charge cut-off voltage of 3.1 V until the current value reached 0.01 C. Thereafter, the lithium-ion battery was stored in a thermostatic chamber at 50° C. for 70 days. The lithium-ion battery after the storage was kept in an environment at 25° C. for 1 hour. Thereafter, constant current discharge was conducted at 25° C. with a current value of 0.2 C and a discharge cut-off voltage of 1.5 V. After a pause of 15 minutes, constant current charge was conducted at 25° C. with a current value of 0.2 C and a discharge cut-off voltage of 3.1 V, followed by constant voltage charge with a charge cut-off voltage of 3.1 V until the current value reached 0.01 C. After a pause of 15 minutes, constant current discharge was conducted at 25° C. with a current value of 1 C and a charge cut-off voltage of 1.5 V, and a discharge capacity (i.e., discharge capacity after storage for 70 days) was measured. Then, a storage stability was calculated according to the following equation. The measurement result is shown in Table 1.

Storage stability at high temperature (%)=(discharge capacity after storage for 70 days/initial discharge capacity)×100

TABLE 1

| Additive | Amount (mass %) | Storage stability (%) | Cycle performance (%) |
|---|---|---|---|
| Example 1 | Tris(hexafluoroisopropyl) borate | 0.5 | 99 | 95 |

TABLE 1-continued

|  | Additive | Amount (mass %) | Storage stability (%) | Cycle performance (%) |
|---|---|---|---|---|
| Example 2 | Tris(hexafluoroisopropyl) borate | 2 | 100 | 98 |
| Example 3 | Tris(hexafluoroisopropyl) borate | 4 | 99 | 97 |
| Comparative Example 1 | — | — | 97 | 93 |
| Comparative Example 2 | Tris(pentafluorophenyl)borane | 2 | 88 | 85 |
| Comparative Example 3 | Tris(trimethylsilyl) borate | 2 | 64 | 63 |
| Comparative Example 4 | Vinylene carbonate | 2 | 87 | 67 |

It was confirmed as shown in Table 1 that Examples 1 to 3 in each of which the non-aqueous electrolyte solution contained a fluorine-containing boric acid ester (tris(hexafluoroisopropyl) borate) were superior in charge and discharge cycle performance and storage stability at a high temperature, as compared to Comparative Examples 1 to 4 in which the non-aqueous electrolyte solution did not contain a fluorine-containing boric acid ester.

Examples 4 to 6, and Comparative Example 5

Lithium-ion batteries were produced in the same manner as in Examples 1 except that the production of a cathode and the preparation of a non-aqueous electrolyte solution were performed as follows. Thereafter, evaluations of the cycle performance and the storage stability at a high temperature were conducted by the methods described below.

(Production of Cathode)

First, 93 parts by mass of a spinel lithium manganese nickel complex oxide as a cathode active material, 5 parts by mass of acetylene black (available from Denka Company Limited) as an electroconductive material, and 2 parts by mass of a copolymer in which acrylic acid and a straight chain ether group were added to a polyacrylonitrile skeleton (Trade name: LSR7, available from Hitachi Chemical Co., Ltd.) as a binder were mixed, and an appropriate amount of N-methyl-2-pyrrolidone was added thereto, followed by kneading, to thereby prepare a pasty cathode mixture (i.e., cathode mixture paste). The cathode mixture was applied on one side of a 20 μm-thick aluminum foil, which was a current collector for a cathode, in a weight of 140 g/m². The coated foil was then subjected to a drying treatment, and subjected to a pressing treatment so that the density of the applied cathode mixture became 2.3 g/cm³, to thereby prepare a sheet-formed cathode. The thus-prepared cathode was cut into a rectangle of 31 mm wide by 46 mm long, to which a cathode collector tab was then attached at the position indicated in FIG. 2.

(Preparation of Non-Aqueous Electrolyte Solution)

A non-aqueous solvent was prepared by mixing ethylene carbonate and dimethyl carbonate at a volume ratio (ethylene carbonate:dimethyl carbonate) of 1:3. Next, $LiPF_6$ as an electrolyte was dissolved in the non-aqueous solvent. The concentration of the electrolyte was adjusted to 1.0 mol/L. Then, an additive as shown in Table 2 was added thereto, to thereby prepare a non-aqueous electrolyte solution. The amount of the additive was adjusted to achieve the content (with respect to the total non-aqueous electrolyte solution as 100% by mass) as shown in Table 2.

(Cycle Performance)

The lithium-ion battery was subjected to constant current charge at 25° C. with a current value of 0.2 C to a charge cut-off voltage of 3.4 V, followed by constant voltage charge with a charge voltage of 3.4 V until the current value reached 0.01 C, using a charge and discharge apparatus (BATTERY TEST UNIT, available from IEM). After a pause of 15 minutes, constant current discharge was conducted with a current value of 0.2 C and a discharge cut-off voltage of 2 V. Charge and discharge under the charging and discharging conditions mentioned above was repeated 2 times. Thereafter, constant current charge was conducted at 25° C. with a current value of 0.2 C and a charge cut-off voltage of 3.8 V, followed by constant voltage charge with a charge voltage of 3.8 V until the current value reached 0.01 C. After a pause of 15 minutes, constant current discharge was conducted with a current value of 0.2 C and a discharge cut-off voltage of 2 V.

Next, constant current charge was conducted at 50° C. with a current value of 1 C and a charge cut-off voltage of 3.8 V, followed by constant voltage charge with a charge voltage of 3.8 V until the current value reached 0.01 C. After a pause of 15 minutes, constant current discharge was conducted with a current value of 1 C and a discharge cut-off voltage of 2 V. The discharge capacity at this time was regarded as the initial discharge capacity. Additionally, a discharge capacity after repeating the above operations 250 times (i.e., discharge capacity after 250 cycles) was measured. Then, a cycle performance (i.e., deterioration rate after 250 cycles) was calculated according to the following equation. The measurement result is shown in Table 2.

Cycle performance (%)=(discharge capacity after 250 cycles/initial discharge capacity)×100

(Storage Stability at High Temperature)

The lithium-ion battery was subjected to constant current charge at 25° C. with a current value of 0.2 C to a charge cut-off voltage of 3.4 V, followed by constant voltage charge with a charge voltage of 3.4 V until the current value reached 0.01 C, using a charge and discharge apparatus (BATTERY TEST UNIT, available from IEM). After a pause of 15 minutes, constant current discharge was conducted with a current value of 0.2 C and a discharge cut-off voltage of 2 V. Charge and discharge under the charging and discharging conditions mentioned above was repeated 2 times. Thereafter, constant current charge was conducted at 25° C. with a current value of 0.2 C and a charge cut-off voltage of 3.8 V, followed by constant voltage charge with a charge voltage of 3.8 V until the current value reached 0.01 C. After a pause of 15 minutes, constant current discharge was conducted with a current value of 0.2 C and a discharge cut-off voltage of 2 V. The discharge capacity at this time was regarded as the initial discharge capacity.

Next, constant current charge was performed at 25° C. with a current value of 0.2 C and a charge cut-off voltage of 3.8 V, followed by constant voltage charge with a charge voltage of 3.8 V until the current value reached 0.01 C. Thereafter, the lithium-ion battery was stored in a thermostatic chamber at 50° C. for 30 days. The lithium-ion battery after the storage was kept in an environment at 25° C. for 1 hour. Thereafter, constant current discharge was conducted at 25° C. with a current value of 0.2 C and a discharge cut-off voltage of 2 V. After a pause of 15 minutes, constant current charge was conducted at 25° C. with a current value of 0.2 C and a discharge cut-off voltage of 3.8 V, followed by constant voltage charge with a charge cut-off voltage of 3.8 V until the current value reached 0.01 C. After a pause of 15 minutes, constant current discharge was conducted at 25° C.

with a current value of 1 C and a charge cut-off voltage of 2 V, and a discharge capacity (i.e., discharge capacity after storage for 30 days) was measured. Then, a storage stability was calculated according to the following equation. The measurement result is shown in Table 2.

Storage stability at a high temperature (%)=(discharge capacity after storage for 30 days/initial discharge capacity)×100

TABLE 2

| | Additive | Amount (mass %) | Storage stability (%) | Cycle performance (%) |
|---|---|---|---|---|
| Example 4 | Tris(hexafluoroisopropyl) borate | 0.5 | 95 | 95 |
| Example 5 | Tris(hexafluoroisopropyl) borate | 1 | 92 | 95 |
| Example 6 | Tris(hexafluoroisopropyl) borate | 2 | 97 | 95 |
| Comparative Example 5 | — | — | 85 | 60 |

It was confirmed as shown in Table 2 that Examples 4 to 6 in each of which the non-aqueous electrolyte solution contained a fluorine-containing boric acid ester (i.e., tris(hexafluoroisopropyl) borate) were superior in charge and discharge cycle performance and storage stability at a high temperature, as compared to Comparative Example 5 in which the non-aqueous electrolyte solution did not contain a fluorine-containing boric acid ester.

The disclosure of Japanese Patent Application No. 2014-212599 is incorporated herein by reference in its entirety. All publications, patent applications, and technical standards mentioned in the present specification are incorporated herein by reference to the same extent as if such individual publication, patent application, or technical standard is specifically and individually indicated to be incorporated by reference.

What is claimed is:

1. A lithium-ion battery, comprising:
    a cathode;
    an anode; and
    a nonaqueous electrolyte solution,
    wherein the cathode comprises a current collector and a cathode mixture applied on at least one side of the current collector,
    wherein the cathode mixture comprises a lithium transition metal oxide as a cathode active material,
    wherein the anode comprises a lithium titanium complex oxide as an anode active material,
    wherein the nonaqueous electrolyte solution comprises a fluorine-containing boric acid ester, and
    wherein a capacity ratio (anode capacity/cathode capacity) of the anode to the cathode is 0.7 or more and less than 1.

2. The lithium-ion battery according to claim 1, wherein the fluorine-containing boric acid ester comprises a compound represented by the following Formula (a):

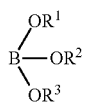

(a)

wherein, in Formula (a), each of $R^1$, $R^2$ and $R^3$ independently represents a hydrocarbon group having 1 to 10 carbon atoms, and at least one of $R^1$, $R^2$, or $R^3$ comprises a fluorine atom.

3. The lithium-ion battery according to claim 1, wherein the fluorine-containing boric acid ester comprises at least one selected from the group consisting of tris(hexafluoroisopropyl) borate, tris(trifluoroethyl) borate, and tris(pentafluorophenyl) borate.

4. The lithium-ion battery according to claim 1, wherein a content of the fluorine-containing boric acid ester is from 0.02% by mass to 5% by mass with respect to a total amount of the nonaqueous electrolyte solution.

5. The lithium-ion battery according to claim 1, wherein the lithium transition metal oxide comprises at least one selected from the group consisting of a spinel lithium manganese oxide (sp-Mn), a layered lithium-nickel-manganese-cobalt complex oxide (NMC), and lithium-manganese-nickel complex oxide (LNMO).

6. The lithium-ion battery according to claim 1, wherein the lithium transition metal oxide comprises a spinel lithium manganese oxide (sp-Mn) and a layered lithium-nickel-manganese-cobalt complex oxide (NMC).

7. The lithium-ion battery according to claim 4, wherein the content of the fluorine-containing boric acid ester is from 0.05% by mass to 5% by mass with respect to a total amount of the nonaqueous electrolyte solution.

8. The lithium-ion battery according to claim 1, wherein the lithium transition metal oxide comprises a spinel lithium manganese oxide (sp-Mn) represented by the following compositional formula (1):

$$Li_{(1+\eta)}Mn_{(2-\lambda)}M'_\lambda O_4 \quad (1)$$

wherein, in the compositional formula (1), $-0.2 \leq \eta \leq 0.2$, $0 \leq \lambda \leq 1$, and M' represents at least one element selected from the group consisting of Mg, Ca, Sr, Al, Ga, Zn, Ti, Cr, Fe, Co, and Cu.

9. The lithium-ion battery according to claim 1, wherein the lithium transition metal oxide comprises a layered lithium-nickel-manganese-cobalt complex oxide (NMC) represented by the following compositional formula (2):

$$Li_{(1+\delta)}Mn_xNi_yCo_{(1-x-y-z)}M_zO_2 \quad (2)$$

wherein, in the compositional formula (2), $-0.15 < \delta < 0.15$, $0.1 < x \leq 0.5$, $0.6 < x+y+z \leq 1.0$, $0 \leq z \leq 0.1$, and M represents at least one element selected from the group consisting of Ti, Zr, Nb, Mo, W, Al, Si, Ga, Ge, and Sn.

10. The lithium-ion battery according to claim 1, wherein the lithium transition metal oxide comprises a combination of a spinel lithium manganese oxide (sp-Mn) represented by the following compositional formula (1) and a layered lithium-nickel-manganese-cobalt complex oxide (NMC) represented by the following compositional formula (2):

$$Li_{(1+\delta)}Mn_{(2-\lambda)}M'_\lambda O_4 \quad (1)$$

wherein, in the compositional formula (1), $-0.2 \leq \eta \leq 0.2$, $0 \leq \lambda \leq 1$, and M' represents at least one element selected from the group consisting of Mg, Ca, Sr, Al, Ga, Zn, Ti, Cr, Fe, Co, and Cu; and $$Li_{(1+\delta)}Mn_xNi_yCo_{(1-x-y-z)}M_zO_2 \quad (2)$$

wherein, in the compositional formula (2), $-0.15 < \delta < 0.15$, $0.1 < x \leq 0.5$, $0.6 < x+y+z \leq 1.0$, $0 \leq z \leq 0.1$, and M represents at least one element selected from the group consisting of Ti, Zr, Nb, Mo, W, Al, Si, Ga, Ge, and Sn.

11. The lithium-ion battery according to claim 1, wherein the lithium transition metal oxide comprises a lithium-manganese-nickel complex oxide having a spinel structure.

12. The lithium-ion battery according to claim 1, wherein the lithium transition metal oxide is represented by LiNi$_x$Mn$_{2-x}$O$_4$ wherein 0.1<X<1.1.

13. The lithium-ion battery according to claim 5, wherein the lithium-manganese-nickel complex oxide (LNMO) comprises LiNi$_{0.5}$Mn$_{1.5}$O$_4$, wherein a part of Mn/Ni sites may be replaced with other metal atom selected from the group consisting of Ti, V, Cr, Fe, Co, Zn, Cu, W, Mg, Al, and Ru.

14. The lithium-ion battery according to claim 1, wherein the lithium titanium complex oxide comprises a spinel lithium titanium complex oxide represented by Li[Li$_{1/3}$Ti$_{5/3}$]O$_4$.

15. The lithium-ion battery according to claim 1, wherein the cathode mixture further comprises a binder, and the binder comprises at least one selected from the group consisting of poly(vinylidene-fluoride) (PVdF) and a copolymer obtained by adding acrylic acid and a straight chain ether group to a polyacrylonitrile skeleton.

16. The lithium-ion battery according to claim 1, wherein the anode mixture further comprises a binder, and the binder comprises at least one selected from the group consisting of poly(vinylidene-fluoride) (PVdF) and a copolymer obtained by adding acrylic acid and a straight chain ether group to a polyacrylonitrile skeleton.

17. The lithium-ion battery according to claim 1, wherein the capacity ratio (anode capacity/cathode capacity) of the anode to the cathode is at least 0.75.

\* \* \* \* \*